(12) United States Patent
Ohkubo et al.

(10) Patent No.: US 8,036,883 B2
(45) Date of Patent: Oct. 11, 2011

(54) ELECTRONIC DEVICE AND A SYSTEM USING THE SAME

(75) Inventors: Norio Ohkubo, Tokyo (JP); Nobuo Sato, Saitama (JP); Yoshihiro Wakisaka, Kokubunji (JP)

(73) Assignee: Hitachi, Ltd., Toyko (JP)

( * ) Notice: Subject to any disclaimer, the term of this patent is extended or adjusted under 35 U.S.C. 154(b) by 999 days.

(21) Appl. No.: 11/984,256

(22) Filed: Nov. 15, 2007

(65) Prior Publication Data

US 2008/0118076 A1 May 22, 2008

(30) Foreign Application Priority Data

Nov. 17, 2006 (JP) ................. 2006-311324

(51) Int. Cl.
*G10L 21/00* (2006.01)
*H04B 1/38* (2006.01)
(52) U.S. Cl. ........ 704/201; 704/270; 704/275; 704/231; 455/41.2; 455/563
(58) Field of Classification Search .................. 704/201, 704/270, 275, 231; 455/41.2, 67.11, 550.1, 455/563
See application file for complete search history.

(56) References Cited

U.S. PATENT DOCUMENTS

| 7,403,895 B2 * | 7/2008 | Iwamoto et al. .............. 704/228 |
| 2007/0030154 A1 | 2/2007 | Aiki et al. | |

FOREIGN PATENT DOCUMENTS

| JP | 2003-339036 | 5/2002 |
| JP | 2006-288619 | 4/2005 |

* cited by examiner

*Primary Examiner* — Minh-Loan T Tran
(74) *Attorney, Agent, or Firm* — Stites & Harbison PLLC; Juan Carlos A. Marquez, Esq.

(57) ABSTRACT

By individuals in an organization possessing a portable node and acquiring sound information, an electronic device and a system that analyze human behavior, group formation, and an activity level of the organization and a system is provided. In an electronic device that has a radio communication unit and a microcomputer, sound is converted into an electrical signal by a microphone, and sound waveform information and characteristic information of sound are obtained using an amplifier, a filter, and an envelope generating circuit. An envelope signal being characteristic information of sound is compared with a reference value by a comparator. Characteristic information of sound when the signal does not reach the reference value, and sound waveform information when greater than the reference value are transmitted from the radio communication unit. The server learns human behavior, group formation; and an activity level of an organization by receiving and analyzing these pieces of information.

20 Claims, 14 Drawing Sheets

FIG.4

|    | 0 | 1 | 2 | 3 | 4 | 5 | 6 | 7 |
|----|---|---|---|---|---|---|---|---|
| 00 | APPLICATION HEADER | DATA TYPE | TRANSMISSION INTERVAL [1] | TRANSMISSION INTERVAL [2] | TRANSMISSION No. | OPTION | CONTINUOUS FRAME END IDENTIFIER | NUMBER OF PIECES OF VOICE DATA |
| 08 | VOICE DATA [1] | VOICE DATA [2] | VOICE DATA [3] | VOICE DATA [4] | VOICE DATA [5] | VOICE DATA [6] | VOICE DATA [7] | VOICE DATA [8] |
| 10 | VOICE DATA [9] | VOICE DATA [10] | VOICE DATA [11] | VOICE DATA [12] | VOICE DATA [13] | VOICE DATA [14] | VOICE DATA [15] | VOICE DATA [16] |
| 18 | VOICE DATA [17] | VOICE DATA [18] | VOICE DATA [19] | VOICE DATA [20] | VOICE DATA [21] | VOICE DATA [22] | VOICE DATA [23] | VOICE DATA [24] |
| 20 | VOICE DATA [25] | VOICE DATA [26] | VOICE DATA [27] | VOICE DATA [28] | VOICE DATA [29] | VOICE DATA [30] | VOICE DATA [31] | VOICE DATA [32] |
| 28 | VOICE DATA [33] | VOICE DATA [34] | VOICE DATA [35] | VOICE DATA [36] | VOICE DATA [37] | VOICE DATA [38] | VOICE DATA [39] | VOICE DATA [40] |
| 30 | VOICE DATA [41] | VOICE DATA [42] | VOICE DATA [43] | VOICE DATA [44] | VOICE DATA [45] | VOICE DATA [46] | VOICE DATA [47] | VOICE DATA [48] |
| 38 | VOICE DATA [49] | VOICE DATA [50] | VOICE DATA [51] | VOICE DATA [52] | VOICE DATA [53] | VOICE DATA [54] | VOICE DATA [55] | VOICE DATA [56] |
| 40 | VOICE DATA [57] | VOICE DATA [58] | VOICE DATA [59] | VOICE DATA [60] | VOICE DATA [61] | VOICE DATA [62] | VOICE DATA [63] | VOICE DATA [64] |
| 48 | VOICE DATA [65] | VOICE DATA [66] | VOICE DATA [67] | VOICE DATA [68] | VOICE DATA [69] | VOICE DATA [70] | VOICE DATA [71] | VOICE DATA [72] |
| 50 | TIME STAMP [1] | TIME STAMP [2] | TIME STAMP [3] | TIME STAMP [4] | RESERVED | RESERVED | RESERVED | RESERVED |

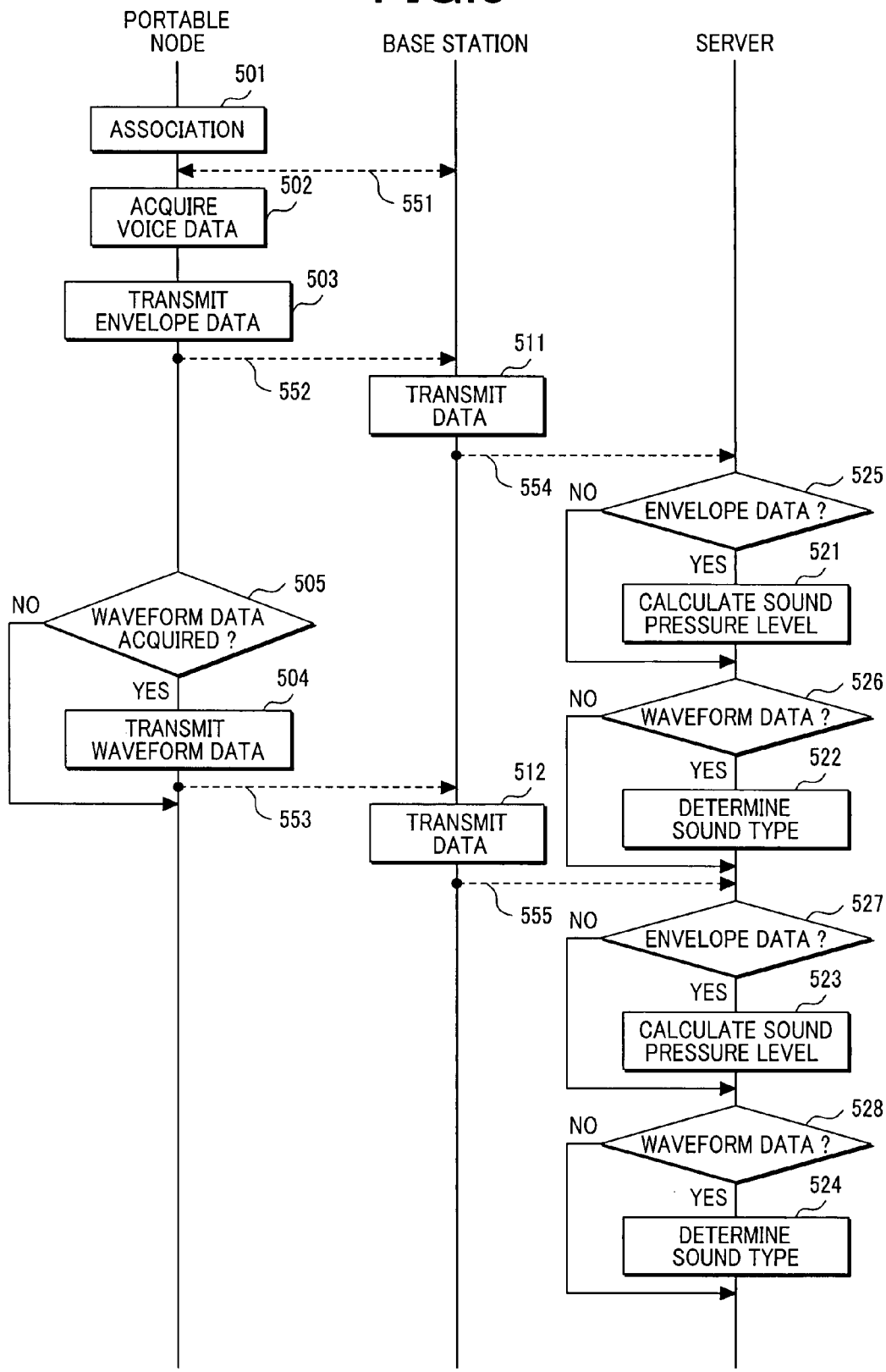

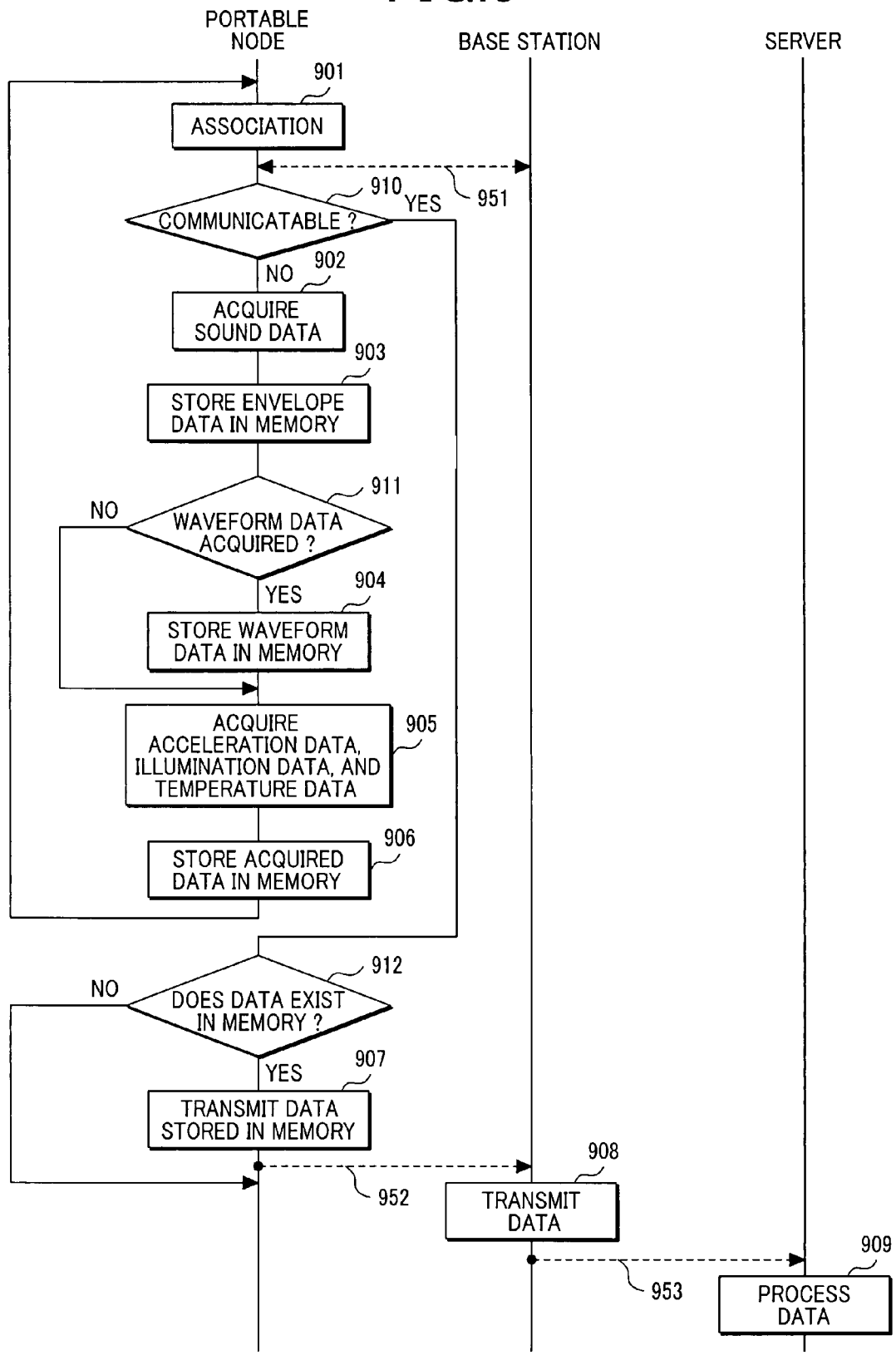

ELECTRONIC DEVICE AND A SYSTEM USING THE SAME

CLAIM OF PRIORITY

The present application claims priority from Japanese application JP 2006-311324 filed on Nov. 17, 2006, the content of which is hereby incorporate by reference into this application.

BACKGROUND OF THE INVENTION

This invention relates to an electronic device suitable for analyzing human behavior and group formation in an organization, and a system using it.

Presently, a sensor node attachable to persons is being developed as a sensor node having a radio communication function available in a sensor net (Japanese Patent Laid-Open No. 2006-288619). To bring such a sensor net into wide practical use, it is important that a sensor node including radio communication functions, sensors, and power supply such as a battery must be maintenance-free and keep transmitting sense data for a long time, and be compact in size. Therefore, though the development of very-small sensor nodes and portable nodes that can be mounted anywhere is in progress, in present situations, it is said that they must be usable without battery replacement for about one year in terms of maintenance costs and usability.

On the other hand, examples of devices that handle human voice include a video conference transmitting device and receiving device, and a voice receiving device (Japanese Patent Laid-Open No. 2003-339036). These devices note that a voice signal has a significant part to which pronunciation and generated voice of actual human speech are inputted, and a noise part that contains meaningless sounds such as natural and mechanical noises, and compress only the significant part to transmit the voice signal.

SUMMARY OF THE INVENTION

Traditional devices that handle voice eliminate the noise part and have not a sufficient construction as devices that analyze human behavior and group formation in an organization. Since voice data is transmitted and received as almost perfect data, power consumption is large, and battery capacity is lacking as carried electronic devices such as sensor nodes, or a heavy battery must be used. Further study is required in terms of maintenance costs and usability.

An object of this invention is to provide an effective electronic device that analyzes human behavior, group formation, and activity levels in an organization. Also, it provides a carried electronic device that saves power consumption by a small amount of information.

To achieve the above-described purpose, this invention provides an electronic device including a radio communication unit. The electronic device includes: an input unit to which a voice signal is inputted; an acquisition unit that acquires sound waveform information from the voice signal; a generating unit that generates characteristic information of sound from the voice signal; and a control unit that controls switching between the sound waveform information and the characteristic information of sound for transmission from the radio communication unit.

Moreover, this invention is an electronic device including a radio communication unit and a control unit. The electronic device includes: an acquisition unit that acquires sound waveform information from an inputted voice signal; and a generating unit that generates characteristic information of sound from the voice signal. The control unit controls switching between the sound waveform information and the characteristic information of sound for transmission from the radio communication unit, depending on whether or not the characteristic information of sound reaches a specific threshold.

Furthermore, this invention provides a system including plural portable nodes each having a radio communication unit and a control unit, and a server connected to the plural portable nodes via a network. Each portable node includes: an acquisition unit that acquires sound waveform information from an inputted voice signal; a generating unit that generates characteristic information of sound from the voice signal; and a control unit that controls switching between the sound waveform information and the characteristic information of sound for transmission from the radio communication unit. The server includes a transmitting/receiving unit that receives the sound waveform information and the characteristic information of sound from plural portable nodes, and a processing unit that uses the received sound waveform information and the characteristic information of sound to analyze the behavior of persons carrying the portable nodes.

According to this invention, by individuals in an organization possessing a portable node and acquiring sound information, an electronic device as a device and a system that analyze human behavior, group formation, and an activity level of the organization and a system can be provided.

Furthermore, according to this invention, since the power consumption of the portable nodes can be reduced, and a small-sized and lightweight battery can be used as a battery of the portable nodes, when individuals in the organization possess, the load of the individuals can be reduced.

By using the electronic device and the system of this invention, measures for improving the productivity of an organization and business efficiency can be taken.

BRIEF DESCRIPTION OF THE DRAWINGS

These and other features, objects and advantages of the present invention will become more apparent from the following description when taken in conjunction with the accompanying drawings wherein:

FIG. 4 is a drawing showing the format of transmission data according to the first embodiment;

FIG. 5 is a sequence diagram of a system of a first embodiment;

FIG. 9 is another sequence diagram in a system of a first embodiment;

DETAILED DESCRIPTION OF THE INVENTION

Hereinafter, preferred embodiments of this invention will be described with reference to the accompanying drawings.

First Embodiment

Figure 1:
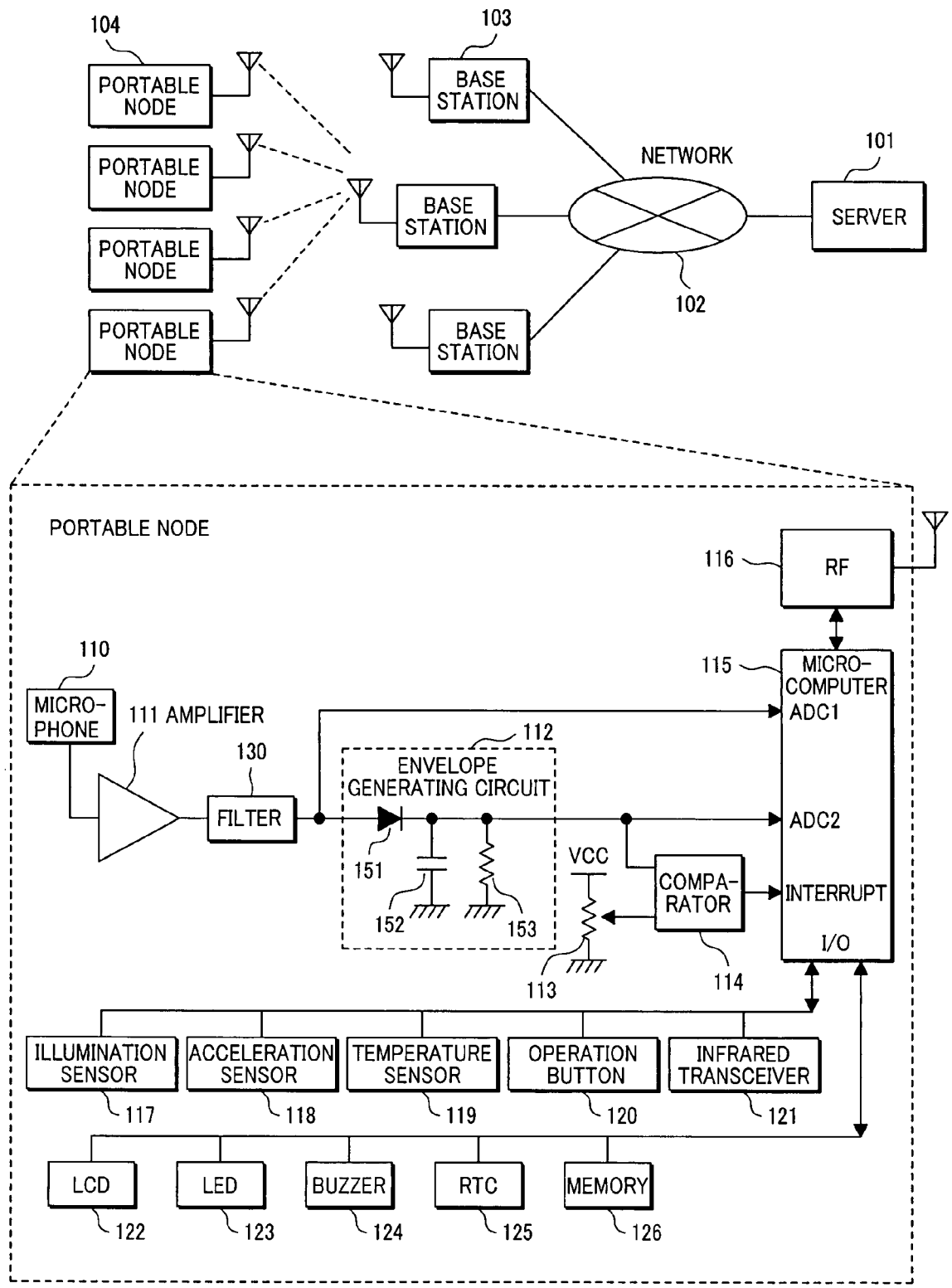
FIG. 1 is a block diagram showing an electronic device according to a first embodiment of this invention and a system using it.

FIG. 1 is a block diagram showing an electronic device according to a first embodiment of this invention and a system using it;

101 designates a server; 102, a network; 103, base stations; and 104, portable nodes of an electronic device.

The server 101 collects, manages, and analyzes information collected to one or plural base stations 103 from plural portable nodes 104 via the network 102, displays the results, and issues commands to the base stations. The server 101, though not shown in terms of a concrete configuration, is configured as a normal computer system that includes a transmitting/receiving unit connected to the network 102, a processing unit, a storage unit, and further a display unit as an output unit. The following describes portable nodes 104 as electronic devices in this embodiment.

In FIG. 1, 110 designates a microphone; 111, an amplifier; 112, an envelope generating circuit; 113, a reference voltage generating circuit; 114, a comparator; 115, a control unit or microcomputer that functions as a processing unit; 116, a radio frequency (RF) circuit as a radio communication unit that exchanges radio frequency signals with an antenna; 117, an illumination sensor; 118, an acceleration sensor; 119, a temperature sensor; 120, an operation button; 121, an infrared ray transceiver; 122, a liquid crystal display (LCD); 123, a light emitting diode (LED); 124, a buzzer or loudspeaker; 125, a real-time clock (RTC); 126, a memory to store data; and 130, a filter circuit.

The portable nodes 104, when carried by a person, collects by the microcomputer 115 information such as sound, voice, temperature, and illumination around the person, and with whom the person is interacting from other people's portable nodes and infrared communication, and the information is transmitted to the base stations by the RF circuit 116. Information transmitted from the base stations can be displayed on the LCD 122, cause the LED 123 to emit light, and cause the buzzer 124 to sound.

The portable node 104 collects-ambient sound and voice as voice signals by the microphone 110, amplifies the electric signals by the amplifier 111, deletes high-frequency components by the filter circuit 130, and inputs the resulting signal to an AD converter incorporated in the microcomputer. An amplification factor of the amplifier 111 may be controlled by the microcomputer. The filter circuit 130, which is intended to acquire sound, may be a low pass filter of about 4 kHz. In other words, the filter circuit 130 or a circuit configuration to the filter circuit 130 constitutes a unit to acquire sound waveform information, and its output is sound waveform information.

Output of the amplifier 111 and the filter circuit 111 is inputted to the envelope generating circuit 112, which generates an envelope signal being characteristic information of sound and inputs it to an AD converter incorporated in the microcomputer 115. After one of the envelope signal being characteristic information of sound, a sound waveform signal being sound waveform information may be selected by a select circuit, as input of the AD converter. The AD converter that collects sound waveform information and characteristic information being an envelope signal does not need to be incorporated in the microcomputer; it may be externally mounted. The sound waveform information and the sound characteristic information may take both forms of analog signal and digital signal before and after the AD converter.

The envelope generating circuit 112 includes a diode 151, a capacitor 152, and a resistor 153. Such a simple circuit is good enough as long as characteristic information indicating the magnitude of sound is obtained as an envelope. In this embodiment, output of the envelope generating circuit 112 is inputted to the comparator 114 and compared with output voltage of the reference voltage generating circuit 113. When a reference voltage is exceeded, the microcomputer is interrupted. Voltages generated by the reference voltage generating circuit 113 may be controlled by the microcomputer.

Transmitting waveforms of ambient sound and voice as unmodified data by radio communication is undesirable in terms of battery size and weight permitted as a carried device because of the large power consumption of radio circuits. For example, when the consumption current of a radio circuit is 20 mA for a battery of 100 mAh, the battery lasts only for five hours, impractically as a carried device.

The following describes the mechanism of transmitting information of ambient sound and voice at a low power consumption in a configuration of this embodiment.

Figure 2A:
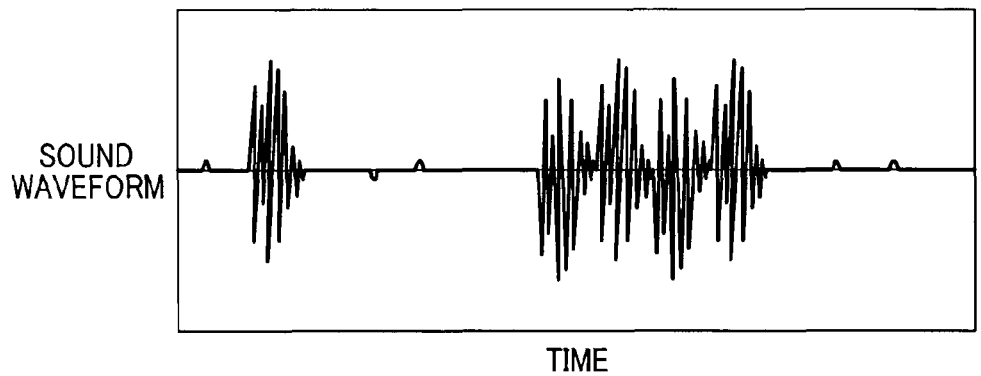
FIG. 2A is a sound waveform chart for explaining a first embodiment.

FIG. 2A shows an example of the waveform of sound. A waveform of sound helps distinguish among environmental sound, impact sound upon collision, human voice, and the like. However, because of an excessively large amount of information, transmitting the sound waveform information all the time is undesirable for power consumption of a carried device.

Figure 2B:
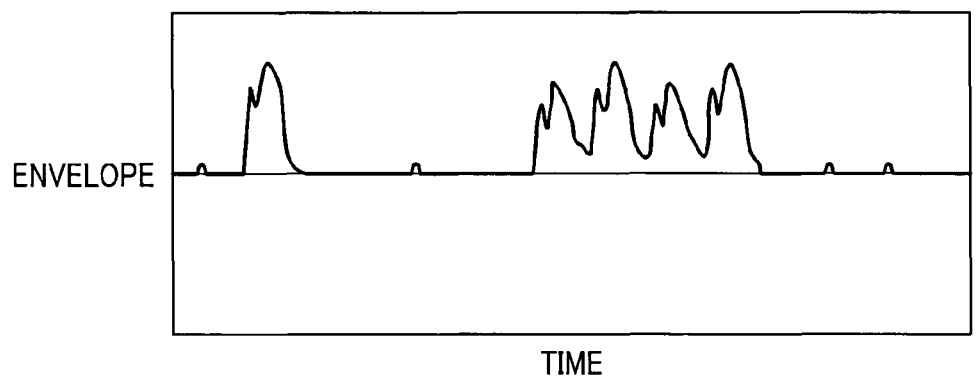
FIG. 2B is a waveform chart of an envelope of a first embodiment.

FIG. 2B shows a signal of an envelope generated from a waveform of sound. The envelope signal being characteristic information of sound does not allow more detailed analysis in comparison with sound waveform information, but helps distinguish among continuous sound, loud sound, small sound, and the like. Since information amounts are smaller than those of sound waveform, obtained data can be transmitted collectively, and power consumption of radio circuits can be reduced.

As a result, we found that acquiring a sound waveform for a short time and an envelope waveform for a long time helps make use of advantages of both and compensate for their respective defects. For example, when a sound waveform is acquired at 8 kHz for 0.5 seconds and an envelope waveform is acquired at 50 Hz for 4.5 seconds, data amounts are about one tenth in comparison with the case where a sound waveform is acquired for five seconds, so that power consumption of radio circuits can be reduced by almost the same level.

Figure 2C:
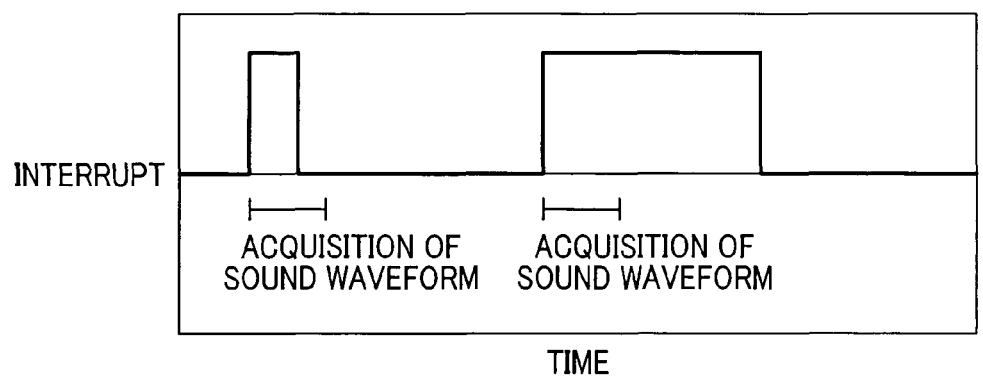
FIG. 2C is a waveform chart of interrupt signal for explaining a first embodiment.

FIG. 2C shows an interrupt signal for acquiring the waveform of sound. In this embodiment, an interrupt signal is a digital signal that goes into a high level when a voltage of an envelope exceeds a set threshold, and a low level when below the set threshold. By acquiring a sound waveform for a set time after the interrupt signal goes into a high level, information of a sound waveform and an envelope waveform can be efficiently obtained.

Thus, by acquiring a sound waveform for a short time and an envelope waveform for a long time, power consumption of radio circuits can be reduced. Processing of acquiring a sound waveform for one second or less and an envelope waveform for one second or more may be performed at the cycle of about 10 seconds. For example, a sound waveform is acquired for about 200 ms.

Figure 3A:
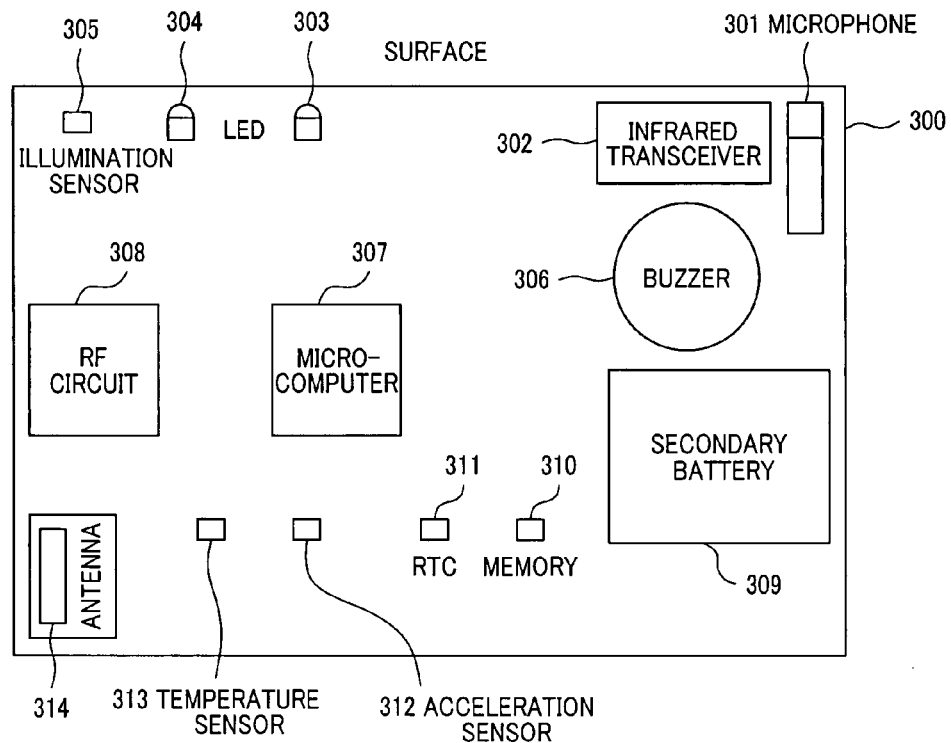
FIG. 3A is a mounting drawing of the surface of a portable node in a first embodiment.
Figure 3B:
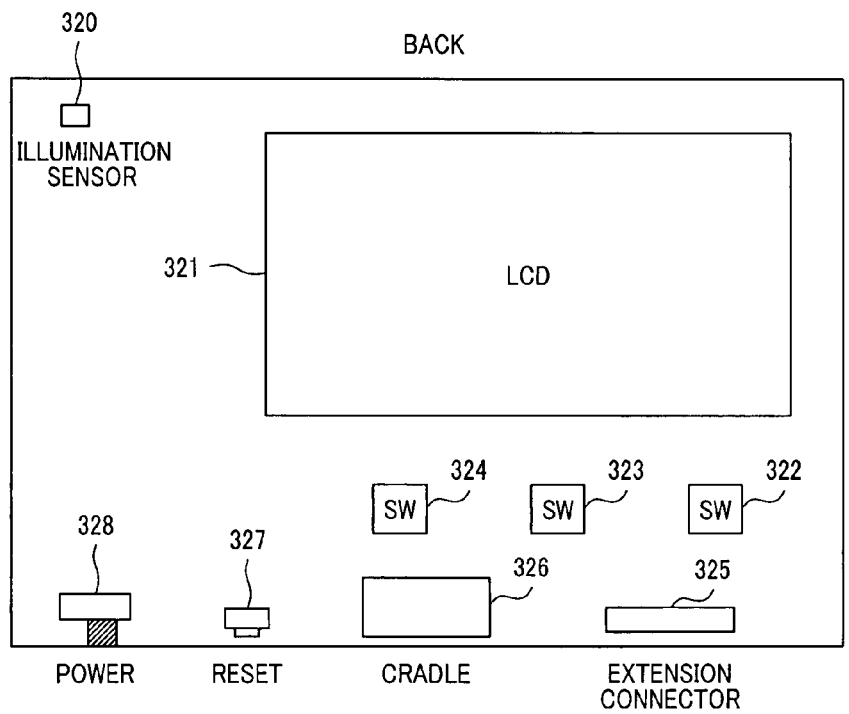
FIG. 3B is a mounting drawing of the back of a portable node in a first embodiment.

FIG. 3 shows a mounting drawing of the portable node 104 of one embodiment of this invention, that is, an electronic device. 300 designates a case; 301, a microphone; 302, an infrared transceiver; 303 and 304, LED; 305, an illumination sensor; 306, a buzzer; 307, a microcomputer; 308, an RF circuit; 309, a secondary battery; 310, a memory; 311, RTC;, 312, an acceleration sensor; 313, a temperature sensor; 314, an antenna; 320, an illumination sensor; 321, LCD; 322, 323, and 324, operation switches; 325, an extension connector; 326, a cradle connector; 327, reset; and 328, a power switch.

Information such as a belonging section and a name is printed on the surface of the case 300 or a seal containing a belonging section, a name, and the like is attached onto the surface of the case 300 so that the case can be carried as a nameplate. It may be suspended from the neck or attached around the chest. Since a thin nameplate is desirable, the nameplate can be made thin by mounting thick parts on one side of a printed board, and thin parts on the other side. In FIG. 3, thin integrated circuit parts such as the microcomputer 307, the RF CIRCUIT 308, the memory 310, RTC 311, and the acceleration sensor 312, and the temperature sensor 313 are mounted on the surface, and thick switches and connectors such as the operation switches 322 to 324, the extension connector 325, the cradle connector 326, the reset switch 327, and the power switch 328 are mounted on the back side.

Thus, since the electronic device mounts the acceleration sensor 312, it can sense impact during collision with a desk and other objects. Meaningless sounds in such a case can be erased by the microcomputer 307, so that waveform information of meaningless sounds is not transmitted. Moreover, since it mounts the infrared transceiver 302, it can communicate with other portable nodes, and for example, can obtain information such as a party with whom the user is interacting.

Furthermore, since the illumination sensors 305 and 320 are mounted on the surface and the back, for example, when the portable node is suspended from the neck, the state of the back facing forward can be sensed, so the buzzer 306 can be sounded, or the LEDs 303 and 304 can be blinked by processing of the microcomputer 307 for notification to the owner.

FIG. 4 is a format drawing showing an example of transmission data in the first embodiment. Data is arranged in a horizontal direction, and vertical numbers are represented in hexadecimal number. The 0-th data is an identification number of application. The first data is an identification number of data type in application. The second and third data are information of transmission interval. The fourth data is the sequential number of a frame to be transmitted of plural frames into which one type of data is split because of the large amount of the data. The fifth data is other incidental data. The sixth data is an identifier indicating whether continuous frame exists. The seventh data is the number of pieces of voice data in one frame. The eighth and subsequent data is voice data, followed by time stamps indicating data acquisition time and reserved data.

During communication, it is determined whether data has been correctly received in units of frames, and when the data has not been correctly received, the data is transmitted again. Therefore, it is undesirable to contain much data in one frame. For example, when information of sound waveforms is sampled at 8 kHz for 0.2 seconds, 1600 pieces of data must be transmitted. Transmitting the data by one frame would cause errors to occur frequently. Therefore, as in this embodiment, a format capable of splitting into plural frames may be adopted. FIG. 4 shows an example of 72 splits.

FIG. 5 is a drawing showing an example of a concrete operation sequence of the electronic device of the above-described first embodiment and a system that uses it. 501-504, 511-512, and 521-524 relate to processing in a sequence diagram, 505 and 525-528 relate to judgment in the sequence diagram, and 551-555 relate to communication in the sequence diagram. The communication is performed based on the IEEE802.15.4 standards, for example.

In this embodiment, in association processing 501 of the portable nodes 104, the portable nodes 104 performs communication 551 with the base station 103 to start communication. Next, in voice data acquisition processing 502, it acquires envelope data being characteristic information of sound, and sound waveform data being sound waveform information if the level of the envelope exceeds a reference voltage. In envelope data transmission processing 503, the portable node performs transmission 552 of the envelope data to the base station. In processing 505, the portable node determines whether it has acquired waveform data. When it has acquired waveform data, it performs transmission 553 of the waveform data. The base station performs transmission 554 and 555 of data transmitted from the portable node to the server. The server determines whether the data is envelope data or waveform data (525-528).

As described in FIGS. 2A and 2B, envelope data is used to calculate sound pressure levels such as loud sound or small sound, while waveform data is used to determine sound types such as environmental sounds, impact sound, and male voice or female voice because of the abundant amount of information. Accordingly, as a result of processing 527, for envelope data, sound levels are calculated (521, 523), and as a result of processing 526, for waveform data, a sound type is determined (522, 524). In FIG. 5, detailed processings such as data confirmation and retransmission in communication are omitted.

By repeating the these processings, it can be determined that conversation is in progress if the sound type is voice, and an activity level of the conversation can be determined from a sound pressure level.

Figure 6:
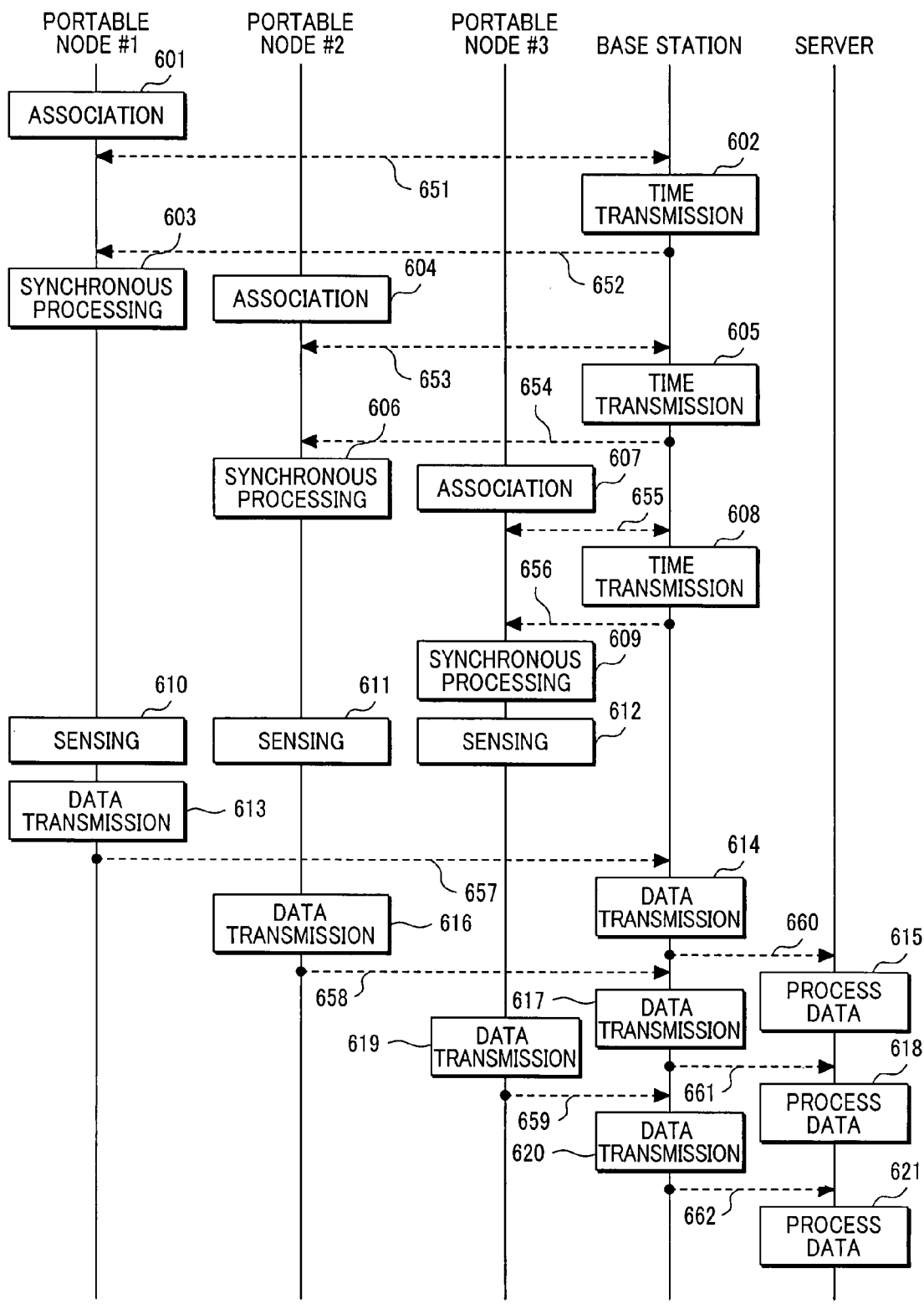
FIG. 6 is a sequence diagram showing an embodiment of synchronous processing of a first embodiment.

FIG. 6 is a drawing showing one embodiment of a synchronous processing sequence of a system in the first embodiment. 601-621 designates processing the sequence diagram and 651-662 designate communication in the sequence diagram. This sequence is processed by the portable nodes and the system that are shown in FIG. 1.

In this embodiment, three portable nodes #1, #2, and #3 communicate with a base station. Any number of portable nodes may communicate with the base station. In association processings 601, 604, and 607 of the portable nodes, they perform communications 651, 653, and 655 with the base station, and start communication. Next, in the base station, time communication processings 602, 605, and 608 are performed for the portable nodes. By synchronous processings 603, 606, and 609, real clocks (RTC) or timers included in the portable nodes are set so that the portable nodes can perform various sensing processings 610, 611, and 612 at the same time. It is desirable that time precision is below one second.

After that, the portable nodes transmit acquired data to the base station by data transmission processings 613, 616, and 619. The base station transmits the data to the server by data transmission processings 614, 617, and 620, and the server analyzes the received data by analysis processings 615, 618, and 621.

Like the sequence of FIG. 5, here, detailed processings such as data confirmation and retransmission are omitted. Synchronous processings 603, 606, and 609 may be performed at anytime without fixing the time.

In this embodiment, after the synchronous processings 603, 606, and 609, the portable nodes perform the sensing processings 610, 611, and 612 at the same time. Thereby, it can be determined by server processing whether persons are forming a group from sound information, and temperature and illumination information.

Figure 7:
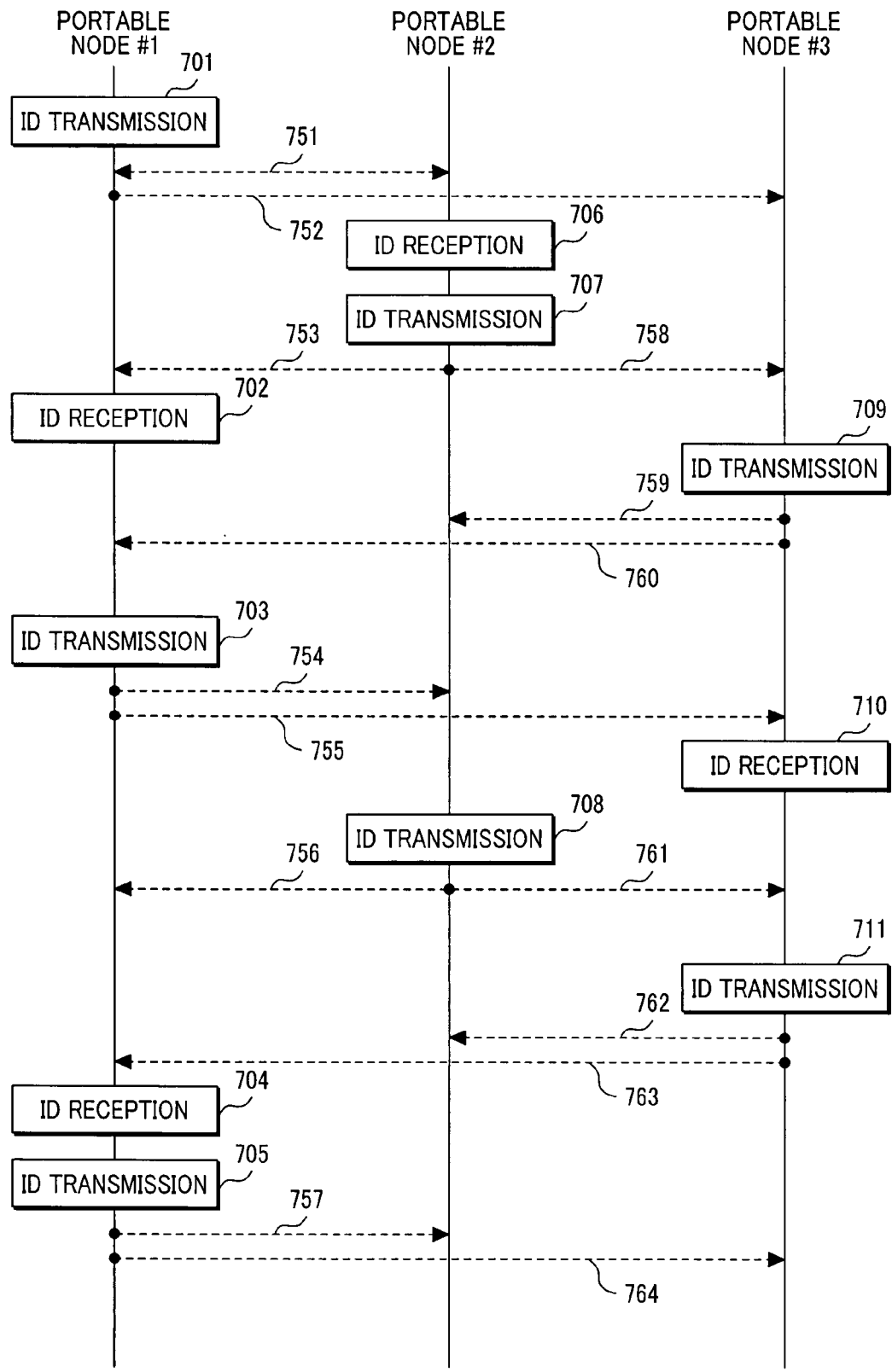
FIG. 7 is a sequence diagram showing one embodiment of ID transmission/reception between portable nodes of a first embodiment.

FIG. 7 is a sequence diagram showing one embodiment of ID transmission/reception between portable nodes 104 in the system of the first embodiment of this invention. 701-711 designate processing in the sequence, and 751-764 designate communication in the sequence diagram. The sequence, like FIGS. 5 and 6, are processed in the portable nodes and the system that are shown in FIG. 1.

This embodiment shows communication processing between the portable nodes in the portable nodes that include an infrared transceiver. Here, three portable nodes #1, #2, and #3 communicate with each other. However, any number of portable nodes may communicate. First, the portable node #1 transmits its identifier (ID) by infrared rays (processing 701). Here, though the portable node #2 receives the ID of the portable node #1, the portable node #3 does not receive the ID of the portable node #1.

Next, the portable node #2 transmits its ID by infrared rays (processing 707). Here, the portable node #1 receives the ID of portable node #2 but the portable node #3 does not receive the ID of the portable node #2. Next, the portable node #3 transmits its ID by infrared rays (processing 709). Here, neither the portable node #1 nor the portable node #2 receives the ID of the portable node #3. In processing up to this, it will be appreciated that the portable nodes #1 and #2 form a group.

Furthermore, the portable node #1 transmits its ID by infrared rays (processing 703). Here, the portable node #3 receives the ID of the portable node #1 but the portable node #2 does not receive the ID of the portable node #1. Next, the portable node #2 transmits its ID by infrared rays (processing 708). Here, neither the portable node #1 nor the portable node #3 receives the ID of the portable node #2. Next, the portable node #3 transmits its ID by infrared rays (processing 711). Here, the portable node #1 receives the ID of the portable node #3 but the portable node #2 does not receive the ID of the portable node #3. In processing up to this, it will be appreciated that the group of the portable nodes #1 and #2 collapses, and a group of the portable nodes #1 and #3 is newly formed.

In the embodiment described above using FIG. 7, by repeating these processings to perform communication processing among the portable nodes by infrared transceivers, the precision of determining whether persons form a group can be increased.

Figure 8:
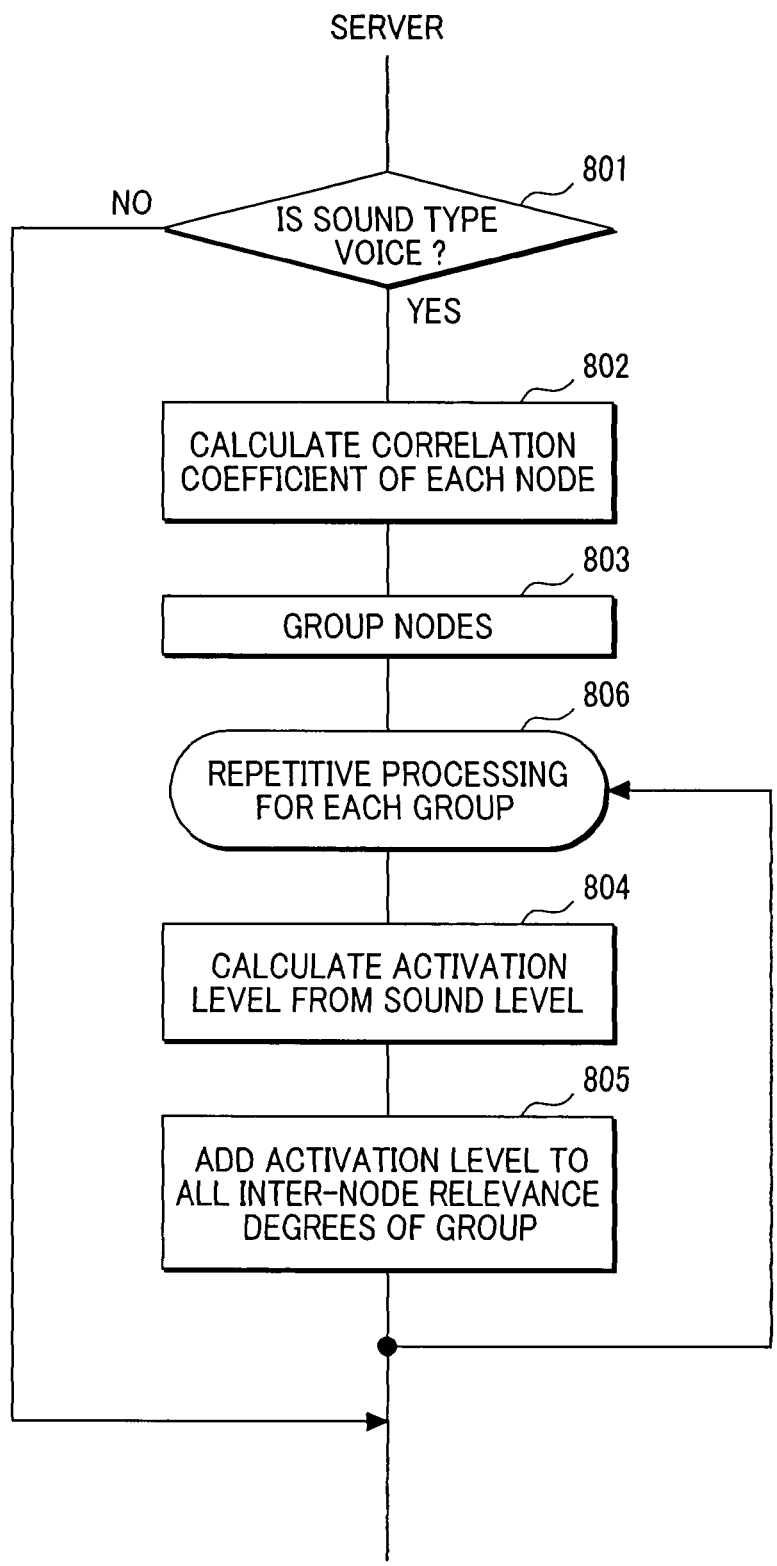
FIG. 8 is a flowchart of server processing in a system of a first embodiment.

FIG. 8 is a flowchart showing one embodiment of server processing in the system of the first embodiment of this invention. As previously described, the server 101 is a normal computer system, which includes a transmitting/receiving unit being a communication interface with the network 102, as well as at least a processing unit and a storage unit, wherein the processing unit executes flowchart processing shown in FIG. 8 by a program loaded into the storage unit. 801 designates determination in the flowchart, 802-805 designate processing in the flowchart, and 806 designates a loop in the flowchart.

In this embodiment, the server 101 uses waveform information of a sound received via the base stations 103 and the network 102 from the portable nodes 104, and determines whether a sound type is voice (determination 801). In the case of voice, it calculates a correlation coefficient of each node to determine the degree of correlation among the portable nodes using the acquired information (processing 802), and groups nodes to classify portable nodes having a correlation (processing 803). Correlation coefficients among the portable nodes are used as inter-node relevance coefficients. For each of formed groups, the server 101 uses characteristic information of the acquired sound to calculate an activity level from a sound pressure level (processing 804) and add the activity level to all inter-node relevance degrees of the group (processing 805).

By repeating these processings, the history of group formation with an activity level of conversation taken into account can be acquired.

FIG. 9 is a drawing showing another embodiment of an operation sequence of the electronic device of the first embodiment and a system using it. 901-909 designate processing in the sequence diagram, 910-912 designate determination in the sequence diagram, and 951-953 designate communication in the sequence diagram.

In this embodiment, in association processing 901 of the portable nodes 104, the portable nodes 104 perform communication 951 with the base stations 103 to start communication. When communication with the base stations is not possible, the portable nodes 104 store envelope data acquired by the voice data acquisition processing 902 in the memory 126 (processing 903), store waveform data, if acquired, in the memory (processing 904), acquire acceleration data, illumination data, and temperature data (processing 905), store the acquired data in the memory (processing 906), and return to the association processing 901.

A delay may be put after the last processing of the repetitive loop. This is because when communication with the base stations is impossible, it is unlikely that communication with the base stations becomes possible during a short period of time. When it is expected that communication with the base stations is impossible for a long time, a large-capacity part may be used as a memory to hold data. A nonvolatile memory may be used.

In determination 910, when communication with the base stations 103 becomes possible, the portable nodes 104 determine whether data exists in the memory 126 (determination 912), and when data exists, transmits the data stored in the memory to the base stations. The base stations transmit the received data to the server 101 in data transmission processing 908, and the server performs data processing 909. The data stored in the memory 126, even when communication with the base stations has become possible, may be transmitted every specific interval, for example, every day.

Figure 10A:
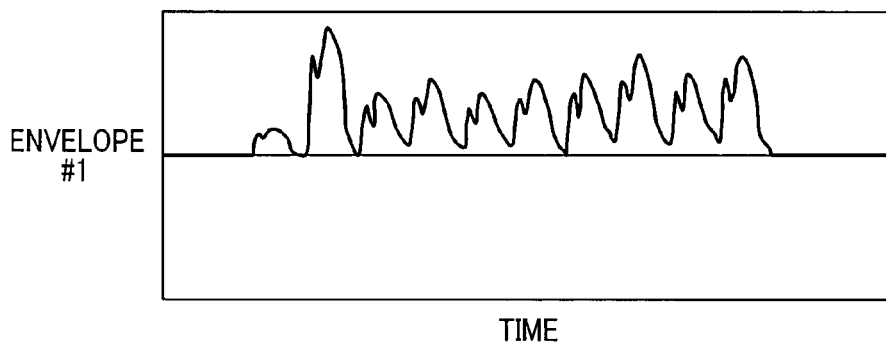
FIG. 10A is a drawing showing envelope data in a first embodiment.
Figure 10B:
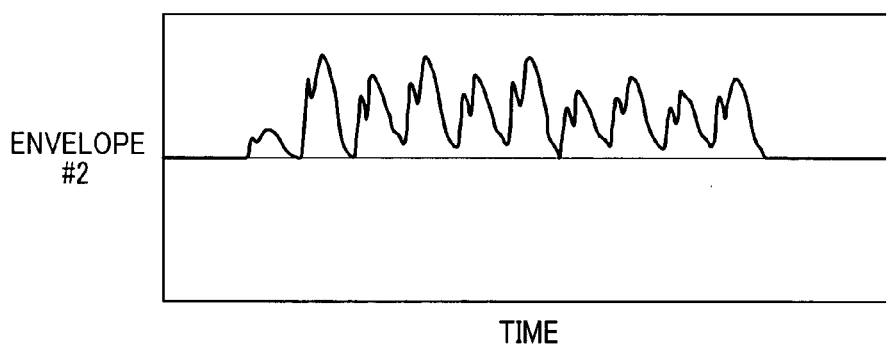
FIG. 10B is a drawing showing other envelope data in a first embodiment.
Figure 10C:
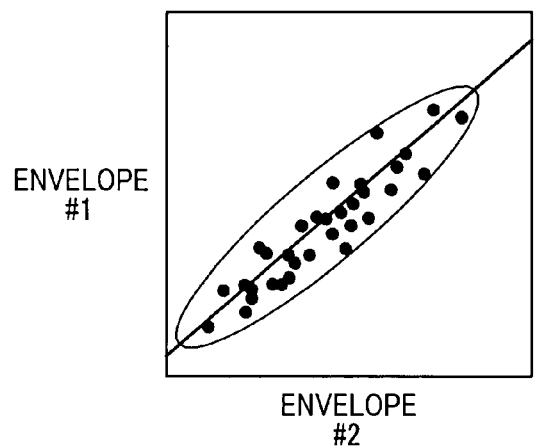
FIG. 10C is a drawing for explaining the correlation of envelope data in a first embodiment.

FIGS. 10A, 10B, and 10C are drawings for explaining one embodiment when a correlation of sound information among the portable nodes in the above-described embodiments is examined. Here, a correlation between an envelope #1 of FIG. 10A and an envelope #2 of FIG. 10B, which are envelope data as characteristic information of sound of two portable nodes, is examined. Their respective times are synchronized by the system synchronous processing described in FIG. 6. FIG.

10C is a drawing showing a result of plotting the values of the envelopes #1 and #2 at the same time. Even if exactly the same data cannot be obtained in each portable node, as shown in FIG. 10C, if a correlation coefficient is high, it is understood that two portable nodes are near each other. If especially loud voices are uttered from each other, it is understood that conversation is in progress. It can be determined that portable nodes are near each other when a correlation coefficient is higher than a specified value, so that the distance between the portable nodes can be determined.

By combining sound information and a face-to-face detection method as typified by the sequence described in the embodiment of FIG. 7, group formation and an activity level of conversation can be analyzed.

Figure 11A:
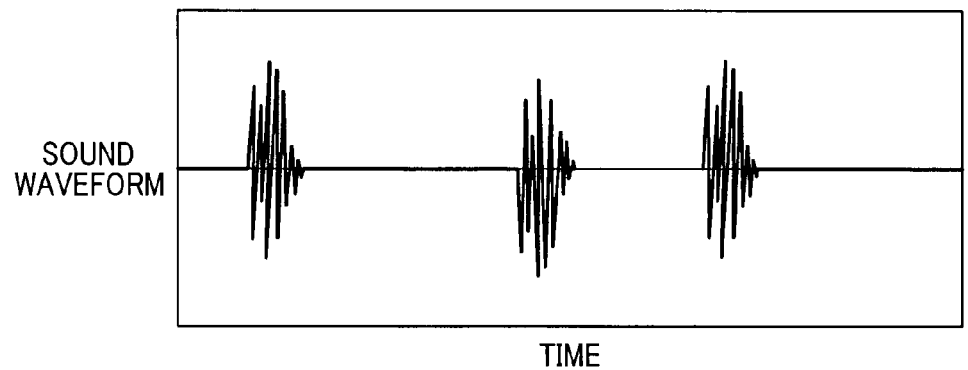
FIG. 11A is a first waveform chart for explaining the analysis of sound in a first embodiment.
Figure 11B:
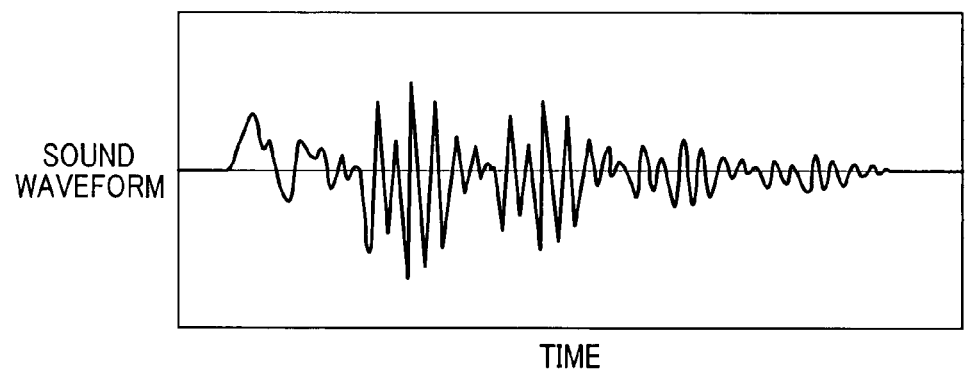
FIG. 11B is a second waveform chart for explaining the analysis of sound in a first embodiment.
Figure 11C:
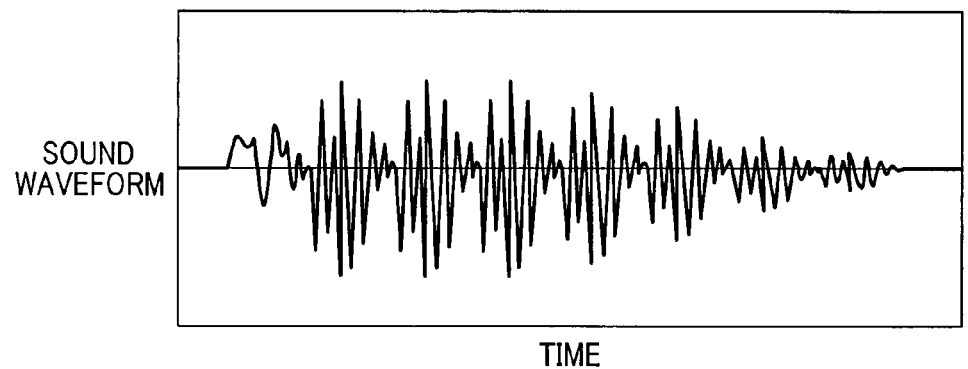
FIG. 11C is a third waveform chart for explaining the analysis of sound in a first embodiment.

FIG. 11 is a waveform chart for explaining one embodiment concerning the analysis of waveform information on sound in the above-described embodiments. It is understood that FIG. 11A shows sporadic sounds. These sounds can be analyzed as impact sounds produced during collision with an object. Like the portable nodes 104 shown in the system of FIG. 1, if the acceleration sensor 118 is included, more detailed analysis can be performed by together using information about changes in acceleration. It can be determined that FIGS. 11B and 11C show human voice by checking vowels, and further from frequency that FIG. 11B shows male voice and FIG. 11C shows female voice.

Figure 12:
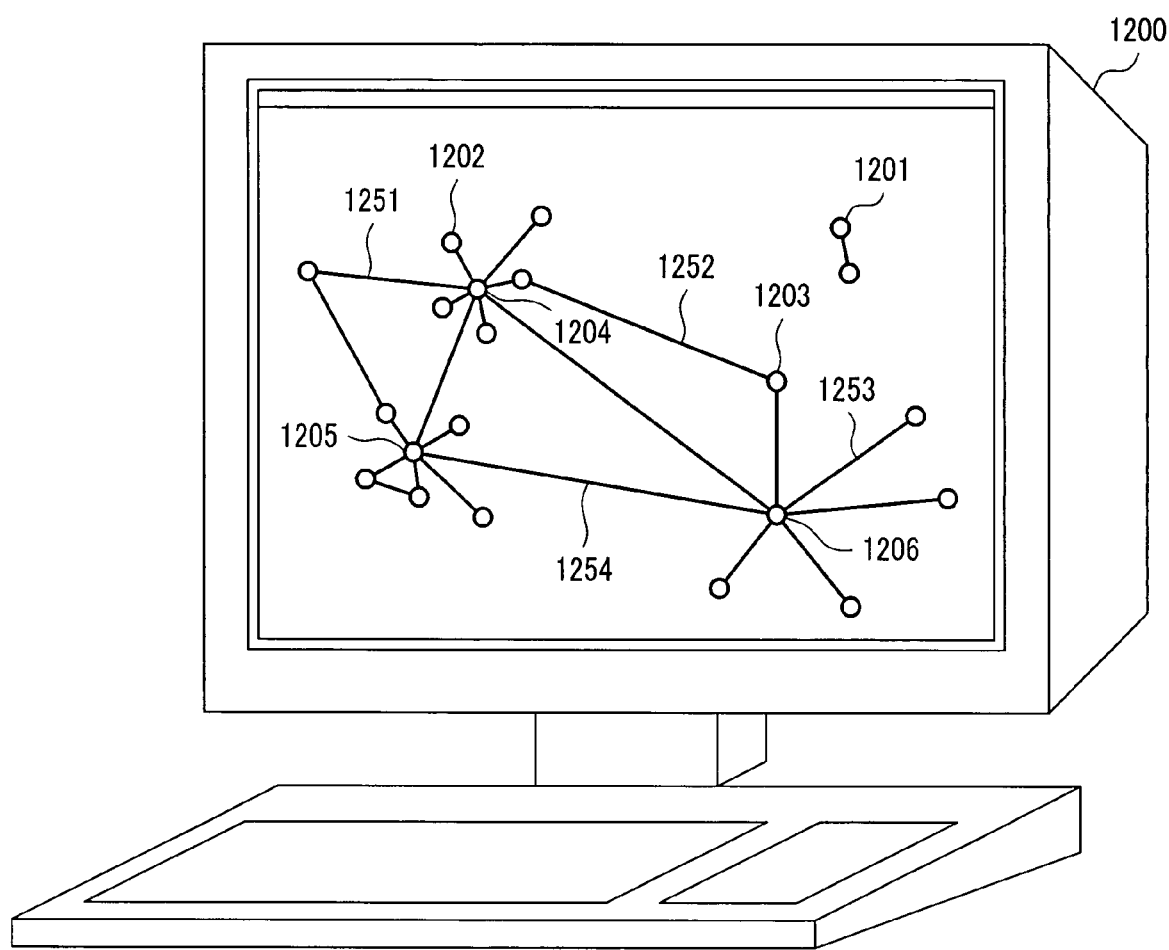
FIG. 12 is a drawing for explaining application of a first embodiment.

FIG. 12 is a drawing for explaining a concrete application of the embodiment described above. 1200 designates a display unit that functions as an output unit of the server 101 being a normal computer system. 1201-1206 designate portable nodes on a display screen. 1251-1254 display inter-node relevance degrees on the display screen by length. It goes without saying that such a display is processed by software by a processing unit not shown within the server 101, based on an inter-node relevance degree calculated by the above-described embodiments.

In the embodiments having been detailed so far, it has been described that human links and group formation can be analyzed. One of the display method is a human network drawing as in this embodiment. Here, the portable nodes 1201-1206 represent persons, and information about their positions on the drawing is meaningless. The length of each line represents a relevance degree. For example, the portable nodes 1204-1206 represent a central existence within the organization and is considered to be a leader. The portable node 1201 is considered existence isolated from the organization. Here, the names of persons may be displayed by clicking the portable nodes 1201-1206 by operation equipment such as a mouse, and relevance degrees may be displayed by clicking the inter-node relevance degrees 1251-1254.

It can be determined quickly from this drawing whether persons to become leaders of the organization are in central positions, whether the degree of the intimacy between the leaders is high, and whether isolated persons are problematic, and feedback to the organization can be made. Thereby, it is possible to take measures for improving the productivity of the organization, and business efficiency. Relevance degrees between portable nodes may be represented not by length but by the thickness of a line.

Second Embodiment

Figure 13:
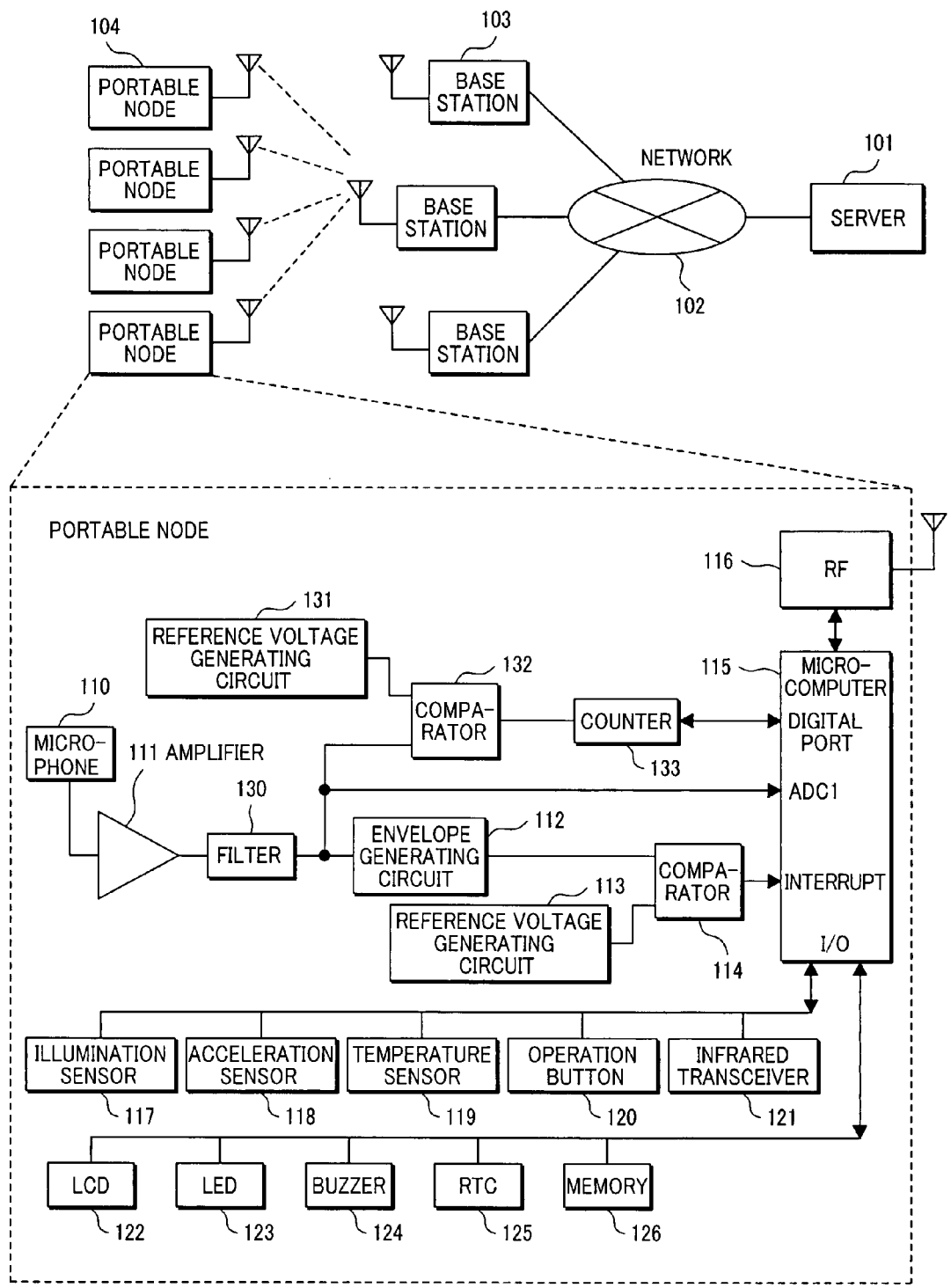
FIG. 13 is a block diagram showing an electronic device according to a second embodiment of this invention and a system using it.

FIG. 13 is a block diagram of a second embodiment of an electronic device of this invention and a system using it. Reference numerals overlapping with FIG. 1 are made identical. A difference from the configuration of FIG. 1 is that comparison with a reference voltage generated by the reference voltage generating circuit 131 is made by a comparator 132, a counter 133 is included to count its output, and control such as reading or resetting the value of the counter 133 can be performed by a microcomputer 115. In this embodiment, as a method of acquiring characteristic information of sound, instead of an envelope, cross count of a reference value generated by the reference voltage generating circuit 131 is taken. That is, the number of times a sound waveform crosses a reference value during measurement for a specified time is used as characteristic information of sound. In this embodiment, the time when the number of times a sound waveform crosses a reference value is acquired using a timer or RTC 125 being a circuit having a function as a clock can be transmitted by radio communication.

In this embodiment, by using a cross count value, in acquiring correlation coefficients between portable nodes, the influence of attenuation of sound in space can be reduced.

As a method of acquiring a count value being information indicating the number of times a reference value is crossed, without adding hardware such as 131-133, as shown in FIG. 13, since a sound waveform is directly inputted to ADC1 of the microcomputer, the count value can be acquired by software. Explanation of this follows.

Figure 14:
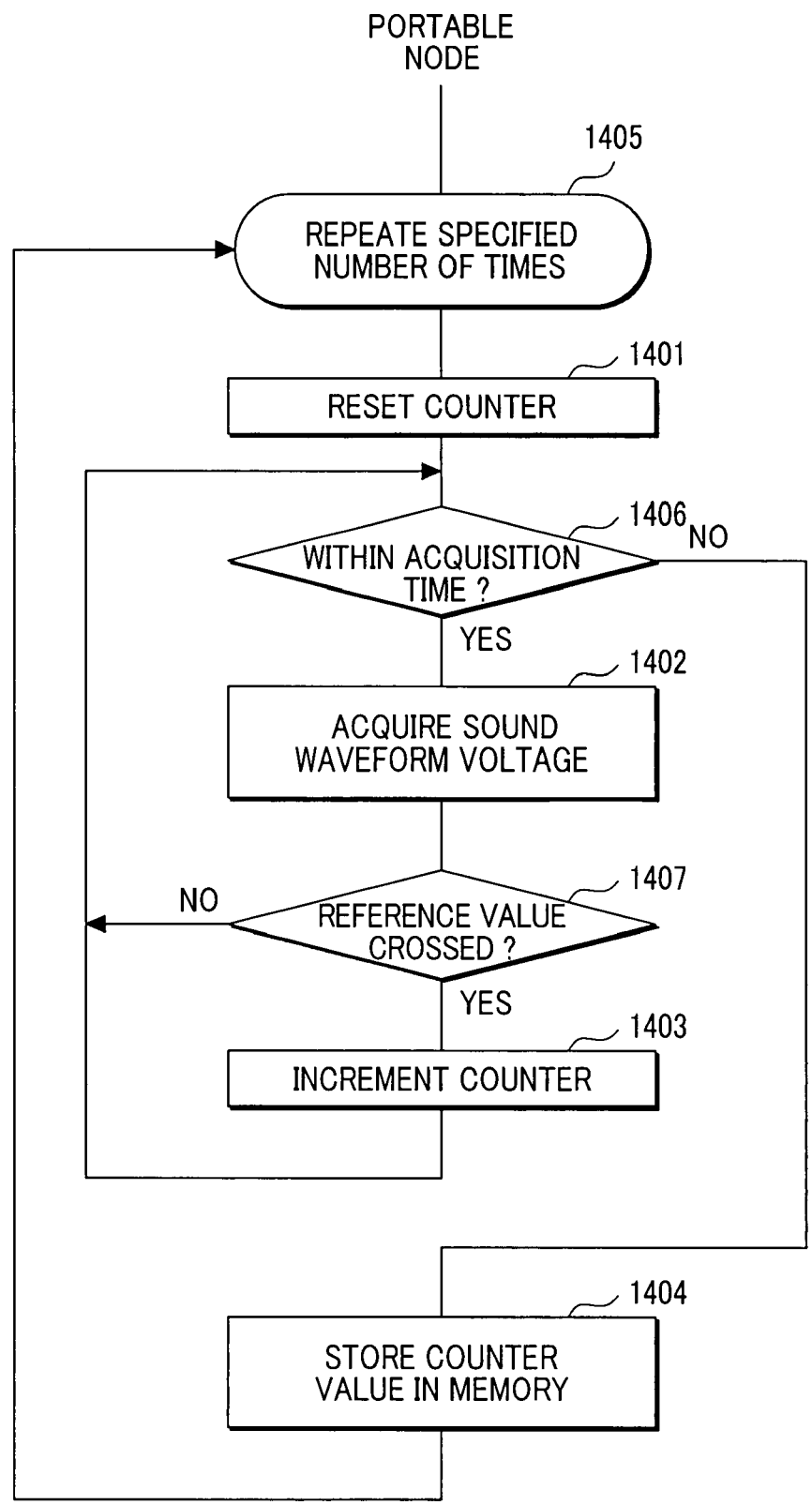
FIG. 14 is a flowchart of processing in a portable node according to a second embodiment node.

FIG. 14 is a flowchart showing a method of acquiring characteristic information of sound by software with the microcomputer 115 in the second embodiment. 1401-1404 designate processings in the flowchart, 1405 designates a loop in the flowchart, and 1406-1407 designate determination in the flowchart.

In this embodiment, in a repetitive loop 1405 by a specified number of times, processing 1401 and subsequent processings are repeated the specified number of times. First, a counter is reset (processing 1401). Within a specified acquisition time, voice waveform voltage acquisition processing 1402, and determination 1407 about whether a specified reference value is crossed are performed. If the reference value is crossed, increment processing 1404 is executed to add one to the counter. When the specified acquisition time is exceeded, the value of the counter is stored in the memory (processing 1404). Information obtained by these processings is sent to the base stations 103 as characteristic information of sound instead of an envelope signal in the first embodiment.

As described above, by using information of the number of times a reference value is crossed, as characteristic information of sound instead of an envelope signal, errors of correlation coefficients due to attenuation of sound in space can be reduced. It goes without saying that an envelop is easily replaced by information of the number of times a reference value is crossed, in the embodiments having been detailed so far.

By the embodiments of this invention having been described above, from sound information, human behavior such as whether conversation is in progress or stopped, and whether active discussions are being made can be acquired. Moreover, it has been shown that analysis of whether a group is formed from correlation coefficients of information with characteristics of sound extracted is possible.

It is apparent that these pieces of information are important in the management of an organization, and by using the electronic device and the system of this invention, measures for improving the productivity of the organization, and business efficiency can be taken.

What is claimed is:

1. An electronic device including a radio communication unit, comprising:
   an input unit to which a voice signal is inputted;

an acquisition unit that acquires sound waveform information from the voice signal;
a generating unit that generates characteristic information of sound from the voice signal; and
a control unit that controls switching between the sound waveform information and the characteristic information of sound for transmission from the radio communication unit.

2. The electronic device according to claim 1,
wherein the generating unit is a circuit that generates and outputs an envelope signal of the voice signal.

3. The electronic device according to claim 2,
wherein the control unit, when the envelope signal outputted from the generating unit exceeds a specific threshold, performs control to transmit the sound waveform information from the radio communication unit.

4. The electronic device according to claim 1,
wherein the generating unit is a circuit that generates and outputs information about the number of times the voice signal crosses a reference value.

5. The electronic device according to claim 4,
wherein the control unit, when the number-of-times information outputted from the generating unit exceeds a specific threshold, performs control to transmit the sound waveform information from the radio communication unit.

6. The electronic device according to claim 1,
wherein the control unit switches between the sound waveform information transmitted from the radio communication unit and the characteristic information of sound, based on the characteristic information of sound.

7. The electronic device according to claim 1, further comprising a storage unit that when the sound waveform information or the characteristic information of sound to be transmitted by the radio communication unit cannot be transmitted, stores the sound waveform information or the characteristic information of sound that cannot be transmitted.

8. An electronic device including a radio communication unit and a control unit, comprising:
an acquisition unit that acquires sound waveform information from an inputted voice signal; and
a generating unit that generates characteristic information of sound from the voice signal,
wherein the control unit controls switching between the characteristic information of sound and the sound waveform information for transmission from the radio communication unit, depending on whether the characteristic information of sound exceeds a specific threshold.

9. The electronic device according to claim 8,
wherein the generating unit is a circuit that generates and outputs an envelope signal of the voice signal.

10. The electronic device according to claim 9,
wherein the control unit, when the envelope signal outputted from the generating unit exceeds the specific threshold, performs control to transmit the sound waveform information.

11. The electronic device according to claim 8,
wherein the generating unit is a circuit that generates and outputs a count value that the voice signal crosses a reference value.

12. The electronic device according to claim 11,
wherein the control unit, when the count value outputted from the generating unit exceeds the specific threshold, performs control to transmit the sound waveform information.

13. The electronic device according to claim 8, further comprising a storage unit that when the sound waveform information or the characteristic information of sound to be transmitted by the radio communication unit cannot be transmitted, stores the sound waveform information or the characteristic information of sound that cannot be transmitted,
wherein, when the radio communication unit has been enabled to transmit, the control unit performs control to transmit the sound waveform information or the characteristic information of sound that is stored in the storage unit.

14. The electronic device according to claim 8, further comprising an acceleration sensor,
wherein the control unit detects by output of the acceleration sensor that the electronic device is impacted, and performs control so as not to transmit the sound waveform information due to the impact.

15. A system comprising a plurality of portable nodes each having a radio communication unit and a control unit, and a server connected to the plurality of portable nodes via a network,
wherein the portable nodes include:
an acquisition unit that acquires sound waveform information from an inputted voice signal;
a generating unit that generates characteristic information of sound from the voice signal; and
a control unit that controls switching between the sound waveform information and the characteristic information of sound for transmission from the radio communication unit, and
wherein the server includes:
a transmitting/receiving unit that receives the sound waveform information and the characteristic information of sound from the portable nodes; and
a processing unit that uses the received sound waveform information and the characteristic information of sound to analyze the behavior of persons carrying the portable nodes.

16. The system according to claim 15,
wherein the control unit, based on the characteristic information of sound, switches between the sound waveform information and the characteristic information of sound that are transmitted from the radio communication unit.

17. The system according to claim 15,
wherein the generating unit generates and outputs an envelope signal of the voice signal, and
wherein the control unit, when the envelope signal outputted from the generating unit exceeds a specific threshold, performs control so as to transmit the sound waveform information from the radio communication unit.

18. The system according to claim 15,
wherein the generating circuit is a circuit that generates and outputs a count value that the voice signal crosses a reference values, and
wherein the control unit, when the count value outputted from the generating unit exceeds a specific threshold, performs control so as to transmit the sound waveform information from the radio communication unit.

19. The system according to claim 15, further comprising a storage unit that when the sound waveform information or the characteristic information of sound to be transmitted to the server by the radio communication unit cannot be transmitted, stores the sound waveform information or the characteristic information of sound that cannot be transmitted,
wherein, when the radio communication unit has been enabled to transmit, the control unit performs control to transmit the sound waveform information or the characteristic information of sound that is stored in the storage unit.

20. The system according to claim 15,
wherein the processing unit of the server takes a correlation between the characteristic information of sound received from the plurality of portable nodes, and determines the distance between the portable nodes from an obtained correlation coefficient.

* * * * *